United States Patent [19]

Berry et al.

[11] Patent Number: 4,850,958
[45] Date of Patent: Jul. 25, 1989

[54] APPARATUS AND METHOD FOR EXTRAPULMONARY BLOOD GAS EXCHANGE

[75] Inventors: Gaylord Berry, Salt Lake City; J. D. Mortensen, Sandy; Larry D. Rigby, Salt Lake City, all of Utah

[73] Assignee: Cardiopulmonics, Inc., Salt Lake City, Utah

[21] Appl. No.: 204,115
[22] Filed: Jun. 8, 1988
[51] Int. Cl.$^4$ .............................................. A61M 5/00
[52] U.S. Cl. ....................................... 604/26; 604/43; 604/53; 604/96
[58] Field of Search ................................... 604/24–26, 604/43, 52, 53, 264, 280, 96–104; 422/45

[56] References Cited

U.S. PATENT DOCUMENTS

| | | | |
|---|---|---|---|
| 3,505,686 | 4/1970 | Bodell | 623/66 |
| 3,794,468 | 2/1974 | Leonard | 23/258.5 |
| 3,856,475 | 12/1974 | Marx . | |
| 4,231,878 | 11/1980 | Esmond | 422/48 |
| 4,239,729 | 12/1980 | Hasegawa et al. | 422/48 |
| 4,265,249 | 5/1981 | Schindler et al. | 128/635 |
| 4,268,279 | 5/1981 | Shindo et al. | 55/16 |
| 4,306,018 | 12/1981 | Kirkpatrick | 435/2 |
| 4,374,802 | 2/1983 | Fukasawa | 422/48 |
| 4,376,095 | 3/1983 | Hasegawa | 422/46 |
| 4,387,711 | 6/1983 | Merry | 128/207.15 |
| 4,576,590 | 3/1986 | Fiddian-Green | 604/26 |
| 4,583,969 | 4/1986 | Mortensen | 604/49 |
| 4,672,287 | 6/1987 | Fiddian-Green | 604/26 |
| 4,717,379 | 1/1988 | Ekaolmer | 604/43 |

FOREIGN PATENT DOCUMENTS 1280481 11/1961 France ................................. 604/101

OTHER PUBLICATIONS

Bodell et al., "A Capillary Membrane Oxygenator," J. Thoracic and Cardiovas. Surg. 46:639 (1963).
Bodell, "An Implantable Artificial Lung," JAMA 191:125 (Jan. 25, 1965).
Galletti et al., "Development of an Implantable Booster Lung," Trans. ASAIO 24:573 (1980).
Tanishita et al., "Augmentation of Gas Transfer with Pulsatile Flow in the Coiled Tube Membrane Oxygenator Design," Trans. ASAIO 26:526 (1980).
Barthelemy et al., "Total Extracorporeal $CO_2$ Removal in a Pumpless Artery-to-Vein Shunt," Trans. ASAIO 28:354 (1982).
Kolobow et al., "Carbon Dioxide and the Membrane Artificial Lung: Their Roles in the Prevention and Treatment of Respiratory Failure," Trans. ASAIO 28:20 (1982).
Phillips et al., "Percutaneous Initiation of Cardiopulmonary Bypass," Annals of Thoracic Surg. 36:223 (1983).
Mortensen, J. D., "An Intravenacaval Blood Gas Exchange (IVCBGE) Device," vol. XXXIII Trans. Am. Soc. Artif. Intern. Organs (1987).
Mortensen, J. D., "An Intra-Venacaval Blood Gas Exchange (IVCBGE) Device," ASAIO Conference (1987).

Primary Examiner—Stephen C. Pellegrino
Attorney, Agent, or Firm—Workman, Nydegger & Jensen

[57] ABSTRACT

An in vivo extrapulmonary blood gas exchange device having a bundle comprised of a plurality of elongated gas permeable tubes being bound at each end and enclosed within a respective air tight proximal and distal chamber. A dual lumen tube having an outer lumen and an inner lumen is situated relative to the gas permeable tubes such that the outer lumen terminates within the proximal chamber and such that the inner lumen terminates within the distal chamber. The apparatus includes means for selectively adjusting the overall, outside diameter of the bundle of gas permeable tubes to provide either a furled, small insertion diameter when inserting the apparatus into the venae cavae of a patient or an unfurled, expanded oxygenation diameter after the apparatus is in place within the venae cavae and the bundle of gas permeable tubes is deployed therein. The apparatus is inserted into the patient through a single incision at one of the right external iliac, common femoral or internal jugular veins. A plurality of crimps along the length of the gas permeable tubes maintain the tubes in a spaced relation one from another such that blood surface contact with the gas permeable tubes is maximized, disturbed flow of blood over the tubes is achieved and laminar blood flow between and around the gas permeable tubes is inhibited.

37 Claims, 4 Drawing Sheets

APPARATUS AND METHOD FOR EXTRAPULMONARY BLOOD GAS EXCHANGE

BACGROUND

1. Field of the Invention

The present invention relates to methods and apparatus for performing extrapulmonary blood gas exchange wherein blood receives oxygen and releases carbon dioxide.

2. The Prior Art

Thousands of patients in hospitals suffer from inadequate blood gas exchange, which includes both inadequate blood oxygenation and inadequate removal of carbon dioxide ($CO_2$). These conditions are commonly caused by varying degrees of respiratory inadequacy usually associated with acute lung illnesses such as pneuminitis, atelectasis, fluid in the lung, or obstuuction of pulmonary ventilation. Various heart and circulatory aliments such as heart disease and shock can adversely affect the flow of blood and thereby also reduce the rate of blood gas exchange.

Currently the most widely used methods of treating these types of blood gas exchange inadequacies involve increasing the flow of oxygen through the lungs by either increasing the oxygen concentration of the inspired gases or by mechanically ventilating the lungs. Both methods result in placing further strain on the lungs, which may be diseased and unable to function at full capacity. In order to allow diseased or injured organs to heal it is generally best to allow these organs a period of rest followed by a gradual increase in activity. The current methods of treating inadequate blood gas exchange, however, force the diseased or damaged lungs to work even harder rather than allowing them a period of rest and recovery.

Various devices have been developed which are capable, at least for a limited period of time, of taking over the gas exchange function of the lungs. Many extracorporeal blood oxygenators are in common use and are employed most frequently during heart surgery. These devices are capaable of providing blood oxygenation sufficient to carry the patient through the surgical procedure. These oxygenators include devices which bubble oxygen into the blood as the blood flows through the device. This is usually followed by a section of the device which defoams the blood to make it acceptable for reinjection into the patient.

Another group of extracorporeal oxygenators employ gas permeable membranes. These devices take many different shapes and configurations; however, the basic concept of operation is the same in all of these devices. Blood flows on one side of the gas permeable membranes while an oxygen rich gas flows on the other side of the membrane. As the blood flows through the device, the oxygen travels across the gas permeable membrane and enters the blood. This allows oxygenation of the blood without actually introducing oxygen bubbles into the blood and without the corresponding need for an extensive defoaming apparatus.

Gas permeable membranes used in such extracorporeal oxygenators are of two types. One type uses a microporous membrane which allows blood gas interface through micropores in the membrane. The other type is a continuous membrane which does not have micropores but which allows blood gas exchange through the membrane without the blood gas interface.

The microporous and bubble oxygenators discussed above are not suited for use outside the setting of a cardiopulmonary bypass procedure, and are thus typically designed for short term extracorporeal use. As a result, these devices are of limited use in the long term intensive care of respiratory patients.

In vivo extrapulmonary blood gas exchange has been attempted in the art. One known device consists of a plurality of small diameter gas permeable tubes connected to headers at each end. The headers are connected on one end to a source of oxygen rich gas and on the other end to an exhaust means.

The apparatus is positioned within the venae cavae by means of a two-step process. First, an incision is made in the patient's femoral or iliac vein or internal jugular vein and in the patient's jugular vein. A radiopaque guide catheter is inserted into the jugular vein and is guided through the superior and inferior venae cavae using a fluoroscope, so as to exit through the incision in the fermoral or iliac vein or internal jugular vein. Second, the device is attached to the guide catheter and is pulled into the vanae cavae by withdrawing the guide catheter from the jugular vein.

While the method of inserting this extrapulmonary blood gas exchange device within a patient's venae canae has been successfully demonstrated, still there are some drawbacks. First, the need for two incisions in the patient's venous system not only increases the complexity of the procedure but also subjects the patient to significant trauma and safety risk. In addition, the need to insert a guide catheter from the patient's jugular vein to the femoral or iliac vein or internal jugular vein exposes the patient to a serious risk of damaging the sensitive intimal tissues of the patient's venous system.

Furthermore, the blood gas exchange device itself must have a small overall diameter to be able to pass through relatively narrow veins such as the jugular vein. As a result, when the device is within the venae cavae, which have a much larger diameter than the jugular vein, the blood flow bypasses the gas permeable tubes. Thus, blood contact with the surface of the gas permeable tubes is reduced.

In an attempt to avoid this problem, a sprial or undulating arrangement of the gas permeable tubes has been used. This increases the blood contact with the gas permeable tube surfaces. Also, the undulating or sprial arrangement of the gas permeable tubes reduces laminar blood flow through the vanae cavae. Laminar blood flow is undesirable because such flow possesses a boundary layer between the bulk flow of the blood and the surface of the gas permeable tubes. This boundary layer of blood significantly reduces gas transfer. The undulating or spiral arrangement of the gas permeable tubes offers limited improvement in performance of the device.

BRIEF SUMMARY AND OBJECTS OF THE INVENTION

The present invention seeks to resolve a number of the problems which have been experienced in the art, as identified above. More specifically, the apparatus and method of this invention constitute an important advance in the art of extrapulmonary blood gas exchange, as evidenced by the following objects and advantages realized by the inventon over the prior art.

One object of the present invention is an apparatus and method for in vivo extrapulmonary blood gas exchange in which oxygen is added to and carbon dioxide is removed from circulating blood without molesting, forcing, or irritating ailing or diseased lungs and which requires only a single venous incision for inserting the device within the patient.

Additionally, it is an object of the present invention to provide an apparatus for in vivo blood oxygenation which may be adjusted to have a narrow diameter for insertion within the patient and which can be expanded to fill the venae cavae during blood oxygenation.

Still an additional object of the present invention is an in vivo extrapulmonary blood gas exchange apparatus and method which more effectively inhibits laminar blood flow through the venae cavae, and around the gas permeable tubes, thus improving gas transfer efficiency by achieving disturbed flow of blood over the gas permeable tubes.

Another object of the present invention is an apparatus for in vivo blood oxygenation which maximizes blood surface contact with the gas permeable tubes, and which is relatively nonthrombogenic and provides efficient blood gas exchange.

Still a further object of the present invention is an apparatus and method for in vivo blood oxygenation which eliminates the risk of introducing an air embolism into the blood stream of the patient.

Additional objects and advantages of the invention will be apparent from the description which follows, or may be learned by the practice of the invention.

Briefly summarized, the foregoing objects and advantages are realized by the apparatus and method of the present invention, which are designed for use on a routine basis and can be used with a more simple surgical procedure. Particularly, the apparatus and method of the present invention can be used instead of the routine lung ventilation or the more invasive extracorporeal membrane oxygenation systems now used to treat patients with inadequate blood gas exchange.

In one embodiment of the present invention, the apparatus comprises a dual lumen tube containing two coaxial lumens. The first lumen opens into a first chamber to which a plurality of gas permeable tubes are attached. The second lumen of the dual lumen tube extends past the first lumen and passes among the gas permeable tubes. Both the second lumen and the gas permeable tubes open into a second chamber. The gas permeable tubes are crimped to form the tubes into a wavy pattern in order to maintain the tubes in a spaced relation one from another so that the blood may flow freely between and around the tubes thereby enhancing blood surface contact with the gas permeable tubes. In addition, the wavy pattern of the gas permeable tubes tend to inhibit laminar blood flow between and around the tubes so as to cause disturbed flow of blood over the tubes.

The apparatus is inserted into a patient through an incision made in either the common femoral vein, external iliac vein or internal jugular vein or internal jugular vein. Before insertion, the second chamber is preferably twisted relative to the first chamber. In this way, the gas permeable tubes are stretched and held tightly together so that the overall diameter of the device is smaller than its untwisted diameter. After insertion into the venae cavae, the second chamber is allowed to unwind so that the gas permeable tubes fill the venae cavae.

The second chamber is twisted relative to the first chamber by means of a stylet which passes through the second lumen and engages the end of the second lumen. Because the second lumen is nonrotatably secured to the second chamber, twisting the stylet simultaneously twists the second chamber. Thus, by twisting the stylet relative to the first chamber, the second chamber is twisted. The stylet is locked so that it cannot unwind during insertion within the patient. After insertion, the stylet is unwound and removed so that the gas permeable tubes fill the venae cavae.

One of either the first or second lumens is connected to a source of oxygen rich gas. The other lumen is connected to an exhaust tube or other means for allowing the gas to flow out of the device. The oxygen rich gas flows into the gas permeable tubes. As venous blood flows around the gas permeable tubes, oxygen passes from the tubes into the blood causing blood oxygenation, and carbon dioxide passes from the blood into the tubes and out of the body. Gas flow through the tubes is augmented and risk of air embolism is eliminated by applying suction to the exhaust tube. The tubes are constructed of a material which allows effecient gas transfer yet is impervious to blood and is also relatively nonthrombogenic.

BRIEF DESCRIPTION OF THE DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only one or more typical embodiments of the invention and are therefore not to be considered limiting of its scope, the presently preferred embodiments and the presently understood best mode of the invention will be described with additional detail through use of the accompanying drawings in which.

DETAILED DESCRIPTION OF THE PREFERRED EMBODIMENTS

Reference is now made to the drawings wherein like parts are designated with like numerals throughout.

Figure 1:
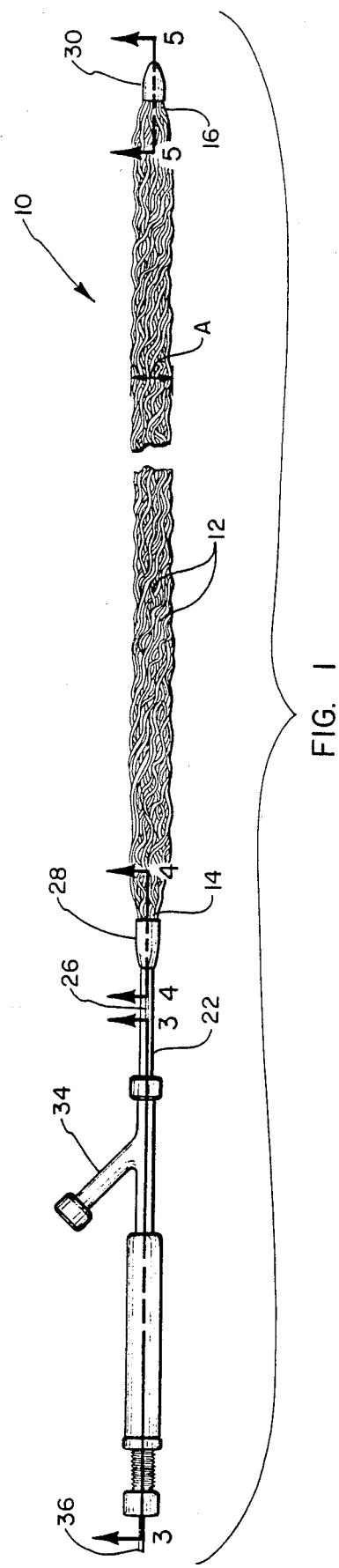
FIG. 1 is a side view of one presently preferred embodiment within the scope of the present invention in which the gas permeable tubes are twisted and elongated to form a small insertion diameter with respect to the outside diameter of the overall bundle of tubes.
Figure 2:
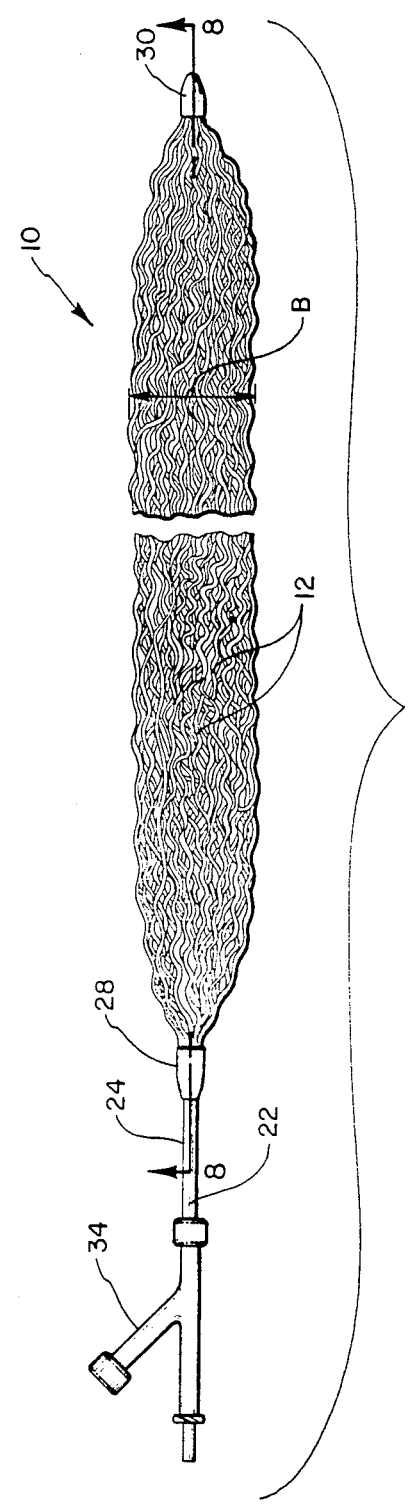
FIG. 2 is a side view of the embodiment of the present invention illustrated in FIG. 1 in which the gas permeable tubes are untwisted to form an expanded oxygenation diameter with respect to the outside diameter of the overall bundle of tubes once they deployed.

Referring first to FIGS. 1 and 2, extrapulmonary blood oxygenator 10 includes a plurality of elongated gas permeable tubes 12 which are bundled together.

Figure 5:
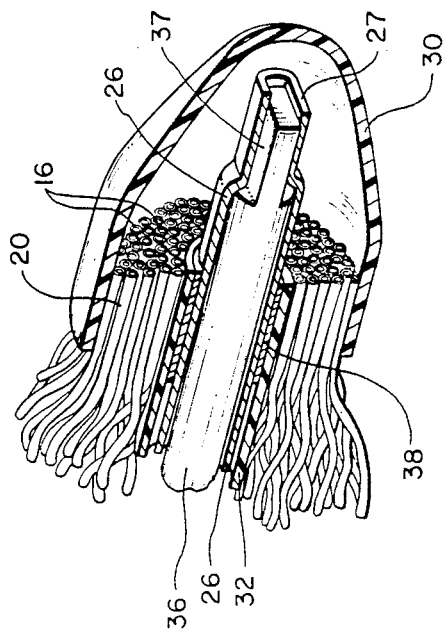
FIG. 5 is an perspective cross-sectional view of a portion of the embodiment illustrated in FIG. 1 taken along line 5—5.
Figure 4:
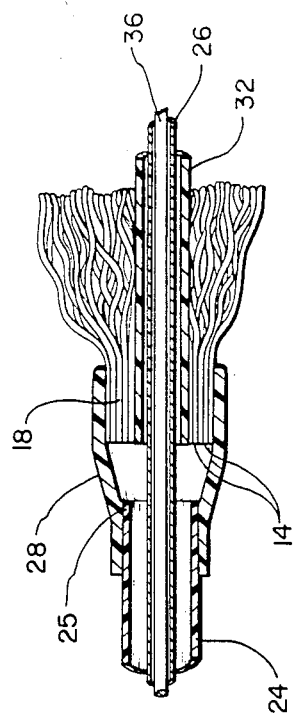
FIG. 4 is an enlarged cross-sectional view of a portion of the embodiment of FIG. 1 taken along line 4—4.

Gas permeable tubes 12 each have a proximal end 14 and a distal end 16. Both the proximal ends and the distal ends of the gas permeable tubes are bound tightly together to form cylindrical ends 18 and 20, as best illustrated in FIGS. 4 and 5.

The apparatus of the present invention is advantageously comprised of a tube means comprising first and second lumens, one of which extends the length of the gas permeable tubes 12, such that one of the lumens terminates adjacent the distal ends 16 of tubes 12, while the other lumen terminates adjacent the proximal ends 14 of tubes 12. As hereinafter more fully explained, this tube means with the first and second lumens, as defined above, eliminates the need for two incisions, rendering insertion into the venae cavae much easier and less traumatic.

Figure 3:
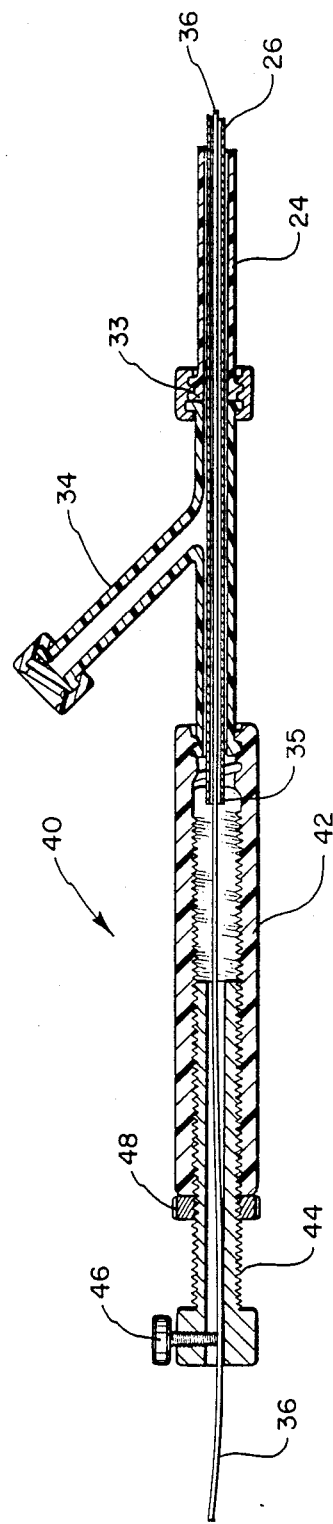
FIG. 3 is an enlarged cross-sectional view of a portion of the embodiment of FIG. 1 taken along line 3—3.
Figure 8:
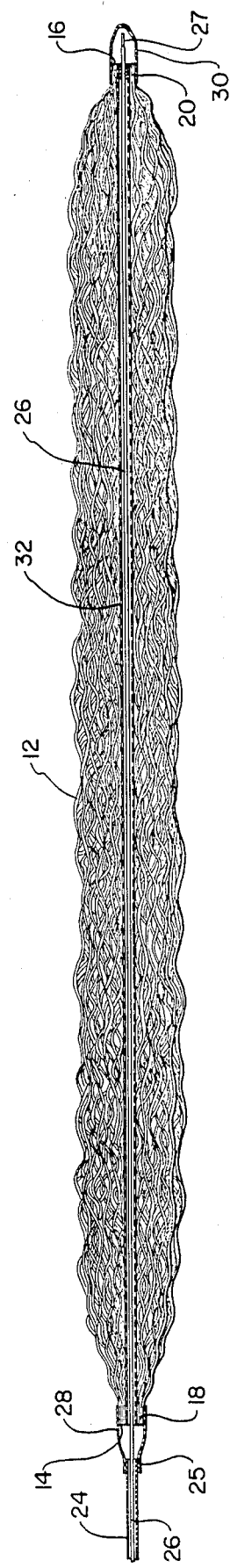
FIG. 8 is a cross-sectional view of the embodiment illustrated in FIG. 2 taken along line 8—8.

As shown best in FIGS. 3 and 8, one manner for providing the described tube means comprises a dual lumen tube 22 having an outer lumen 24 and an inner lumen 26. The inner lumen 26 preferably runs coaxially through the outer lumen 24. The dual lumen tube 22 is situated relative to the gas permeable tubes such that the distal end 25 (see FIG. 8) of the outer lumen 24 terminates adjacent to the proximal ends 14 of the gas permeable tubes 12. The inner lumen 26 extends past the distal end 25 of the outer lumen 24 such that the distal end 27 of the inner lumen 26 terminates adjacent to the distal ends 16 of the gas permeable tubes 12.

The apparatus of the present invention further comprises means for introducing oxygen from a first lumen into the gas permeable tubes, and means for collecting carbon dioxide as it exits the gas permeable tubes and introducing the carbon dioxide into a second lumen for removal from the apparatus.

One way of providing the functions of introducing oxygen into the gas permeable tubes and thereafter collecting carbon dioxide as it exits the gas permeable tubes is achieved by a means for enclosing the proximal and distal ends of the gas permeable tubes so as to form airtight chambers. By also enclosing the distal ends of the outer and inner lumen within the airtight chambers, the gas permeable tubes are in gaseous communication with the outer and inner lumens.

As illustrated in FIGS. 4 and 5, one way of providing the described means for enclosing the proximal ends 14 of the gas permeable tubes 12 comprises a proximal chamber 28 which also encloses the distal end 25 of outer lumen 24. The proximal chamber 28 is airtight such that the outer lumen 24 is in gaseous communication with the bound proximal ends 14 of the gas permeable tubes.

Similarly, one method for providing the described means for enclosing the distal ends 16 of gas permeable tubes 12 comprises distal chamber 30 which also encloses the distal end 27 of inner lumen 26. The distal chamber 30 is airtight such that the bound distal ends 16 of the gas permeable tubes 12 are in gaseous communication with the inner lumen 26.

In the embodiment illustrated in FIGS. 4 and 5, a spacer lumen 32 is bound to both the proximal and distal cylindrical ends 18 and 20. Spacer lumen 32 extends between the proximal and distal chambers 28 and 30, and the spacer lumen terminates at approximately the same point the proximal ends 14 and distal ends 16 of the gas permeable tubes terminate.

The ends of the gas permeable tubes and the spacer lumen 32 are preferably bound with a potting agent that will produce and airtight bond between the gas permeable tubes and the spacer lumen 32. Airtightness is a critical safety consideration because the apparatus should not introduce air bubbles within the blood stream. If air bubbles are introduced into the patient's blood stream, there is a serious risk of air embolism formation which can be fatal.

Other factors to be considered in selecting a suitable potting compound are its viscosity, surface tension, wettability, and spreadability. Polyurethane is one presently preferred potting compound for binding the ends of the gas permeable tubes. Other suitable compounds include epoxies, silicones, and other thermosetting resins.

As illustrated in FIG. 5, the inner lumen 26 is bound to spacer lumen 32 with bonding agent 38. In this way, the inner lumen is nonrotatably bound to distal cylindrical end 20. Bonding agent 38 is preferably a material capable of bonding the inner lumen 26 to the spacer lumen 32. The bonding agent should be able to maintain an airtight seal despite a warm and humid in vivo environment. In addition, the bonding agent 38 should be able to withstand sterilization. One presently preferred bonding agent is an epoxy resin.

Referring now to FIG. 3, a connector 34 is removably attached to the proximal end of dual lumen tube 22. Connector 34 permits the proximal end 33 of outer lumen 24 and the proximal end 35 of inner lumen 26 to be coupled either to a source of oxygen enriched gas or to a vacuum or other exhaust means.

The embodiment of the present invention illustrated in FIGS. 1 and 2 is designed for in vivo extrapulmonary blood gas exchange within the venae cavae of a patient. To use the apparatus in vivo, it should preferably have an overall outside diameter with respect to the bundle of gas permeable tubes 12 that is suffeciently small to be inserted within the venae cavae through a peripheral vein, yet also have an overall outside diameter of the bundle that is sufficiently large to fill the venae cavae cross-section once tubes 12 are deployed therein. To achieve both of these objectives, the overall diameter of the gas permeable tubes 12 may be selectively adjusted to provide either a small insertion diameter when inserting the apparatus within the venae cavae or an expanded oxygenation diameter after the apparatus is in place within the venae cavae.

To selectively adjust the overall outside diameter of the bundle of gas permeable tubes 12, the gas permeable tubes are twisted and elongated. The overall outside diameter of the bundle of gas permeable tubes is adjusted by twisting either the proximal cylindrical end 18 or the distal cylindrical end 20 relative to the other.

The means for selectively adjusting the overall diameter of the gas permeable tubes comprises means for engaging the distal end 27 of the inner lumen 26. In this way, the distal cylindrical end 20 may be selectively twisted or held stationary relative to the proximal cylindrical end 18.

The means for selectively adjusting the overall diameter of the gas permeable tubes further comprises means for twisting the gas permeable tubes while holding either the distal or proximal cylindrical ends essentially stationary relative to the other. This may be accomplished by twisting the engaging means while holding the proximal cylindrical end 18 relatively stationary.

One manner for providing the described means for selectively adjusting the overall diameter of the gas permeable tubes is shown in FIGS. 3 and 5. The means for engaging the distal end 27 of the inner lumen 26 and stretching the tubes 12 comprises a removable stylet 36, and the means for twisting the gas permeable tubes comprises a twisting mechanism 40 which facilitates twisting the stylet 36.

The distal end 37 of the stylet 36 has a configuration which engages the distal end 27 of the inner lumen 26. In FIG. 5, the stylet is constructed to have two flat parallel surfaces which engage corresponding flat parallel surfaces on the inner lumen. It will be appreciated that other means for engaging the distal end of the inner lumen would also be suitable.

Both the distal end of the inner lumen and the stylet are preferably constructed of a material sufficiently strong to permit mutual engagement. In one currently preferred embodiment within the scope of the present invention, the stylet 36 is constructed out of a metal rod and the inner lumen 26 is constructed out of stainless steel. A stainless steel inner lumen provides more structural support for the gas permeable tubes 12 than spacer lumen 32 standing alone. In this way, the apparatus is readily maintained in the proper position within the venae cavae.

In an alternative embodiment within the scope of the present invention, only the distal end of the inner lumen 26 is constructed of stainless steel. The stainless steel portion terminates just proximal of bonding agent 38. The remainder of the inner lumen is formed by an extension of spacer lumen 32 past proximal chamber 28 such that spacer lumen 32 extends coaxially within outer lumen 24.

Because the distal end 27 of the inner lumen 26 is nonrotatably bound to distal cylindrical end 20, any twisting of the distal end 27 of the inner lumen 26 simultaneously twists the bound distal ends of the gas permeable tubes, and elongates the tubes by slightly stretching them. Thus, it stylet 36 is twisted while holding proximal cylindrical end 18 relatively stationary, then the gas permeable tubes 12 are twisted and elongated.

To achieve the foregoing, a twisting mechanism 40 is used to twist the stylet 36 (thereby twisting the distal cylindrical end 20) while holding the proximal cylindrical end 18 relatively stationary. As shown in FIG. 3, twisting mechanism 40 includes stationary member 42 and twisting member 44. The stationary member 42 is removably attached to connector 34 which is secured to outer lumen 24. Because the outer lumen 24 is bound to proximal chamber 28, which is further bound to proximal cylindrical end 18, the proximal cuylindrical end may be held relatively stationary by holding stationary member 42 relatively stationary.

Twisting member 44 includes a screw 46 for selectively securing the stylet 36 to the twisting member. The twisting member 44 is rotatably engaged with the stationary member 42. Once the stylet 36 has engaged the distal end 27 of inner lumen 26 and is secured to twisting member 44, twisting the twisting member relative to the stationary member simultaneously twists distal cylindrical end 20 relative to proximal cylindrical end 18.

The twisting member 44 also includes a locking ring 48 which may be threadably moved along the length of the twisting member to lock the relative positions of the twisting and stationary members. Thus, after the gas permeable tubes have been tightly twisted and elongated, as shown in FIG. 1, the locking ring permits the gas permeable tubes to remain twisted and elongated while the apparatus is inserted into the patient. Diameter "A" of FIG. 1 represents an insertion diameter sufficiently small to enable the apparatus to be inserted within the venae cavae through a small peripheral vein.

Figure 7:
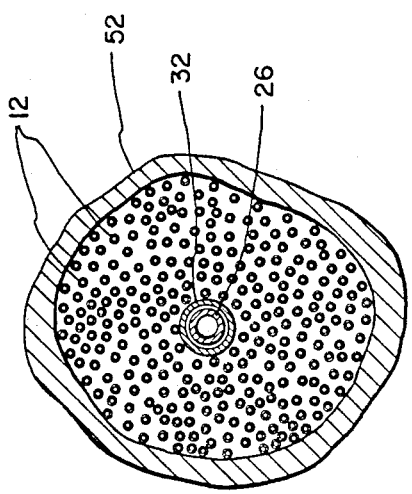
FIG. 7 is an enlarged cross-sectional view of the embodiment of the present invention within the inferior vena cava as illustrated in FIG. 6 taken along line 7—7.

After insertion within the venae cavae of the patient, locking ring 48 is released so that the gas permeable tubes may be untwisted, as shown in FIG. 2. Diameter "B" of FIG. 2 represents an expanded oxygenation diameter sufficiently large that the gas permeable tubes loosely fill the cross-section area of the venae cavae as shown in FIG. 7. Screw 46 is then released to permit removal of the stylet from within the inner lumen. The twisting mechanism 40 can then be removed from connector 34.

Because the spacer lumen 32 is bound to both the proximal cylindrical end 18 and distal cylindrical end 20, the spacer lumen is twisted as the gas permeable tubes are twisted. Therefore, the spacer lumen should preferably be constructed of a material which may be twisted. In addition, the spacer lumen should be constructed of a material which can be securely bound with the proximal and distal cylindrical ends.

One presently preferred material for constructing the spacer lumen 32 is polyurethane due to its high elasticity and compatibility with the polyurethane potting compound. Other possible suitable materials for constructing the spacer lumen are polyvinyl chloride and silicone. However, the choice of spacer lumen determines to a large extent what potting compound will be suitable. For example, if spacer lumen 32 is constructed of silicone, it would be necessary to use a silicone potting compound in order to form an adequate airtight bond between the ends of the gas permeable tubes and the spacer lumen.

Because gas transfer is a primary function of the apparatus, the gas transfer surface area in contact with the blood is preferably maximized. To increase the gas transfer surface area without unduly increasing the size of the apparatus, a large number of very small diameter gas permeable tubes are used. In addition, the gas permeable tubes are preferably thin-walled in order to enhance gas permeability.

The total number of tubes and the cross-sectional diameter of each tube are both considered in determining a preferred operating embodiment of the in vivo apparatus. The apparatus must be small enough to be inserted into the venae cavae through a smaller peripheral vein, yet have a large enough gas transfer surface to achieve the desired blood gas exchange. Thus, as the cross-sectional diameter of the gas permeable tubes increases, the total number of tubes which can be used decreases.

Each gas permeable tube 12 preferably has an outside diameter in the range from about 200 microns to about 350 microns. Depending upon the size of the patient (i.e., whether infant or adult) and the amount of oxygenation therefore required, the number of gas permeable tubes 12 will vary. For example, in applications for the apparatuses to be used with infants, typically the apparatus would contain approximately 90 tubes. For applications of the apparatus which are intended for use with adults, up to 1500 tubes may be used.

The gas permeable tubes are preferably maintained in a spaced relation one from another such that the blood surface contact with the gas permeable tubes is maximized and such that laminar blood flow between and around the tubes is inhibited and disturbed blood flow over the tubes is achieved. To achieve this in one preferred embodiment of the present invention, the gas permeable tubes include a plurality of crimps which form the tubes 12 into a wavy pattern. The crimps of the gas permeable tubes 12 also aid in permitting the tubes to be slightly stretched as they are twisted so as to elongate the bundle of tubes 12 when it is desired to narrow the overall outside diameter of the bundle of 12's for purposes of forming the insertion diameter as described above.

Since the gas permeable tubes will be in contact with flowing blood, it is critical to minimize thrombosis formation. As a result, the gas permeable tubes are preferably constructed of a thrombo-resistant material. In one embodiment of the present invention, the gas permeable tubes include a support material constructed of polypropylene coated with a thin siloxane polymer. The siloxane is relatively nonthrombogenic. However, in a preferred embodiment the siloxane surface is coated with thrombo-resistant materials to further minimized thrombosis formation.

Figure 6:
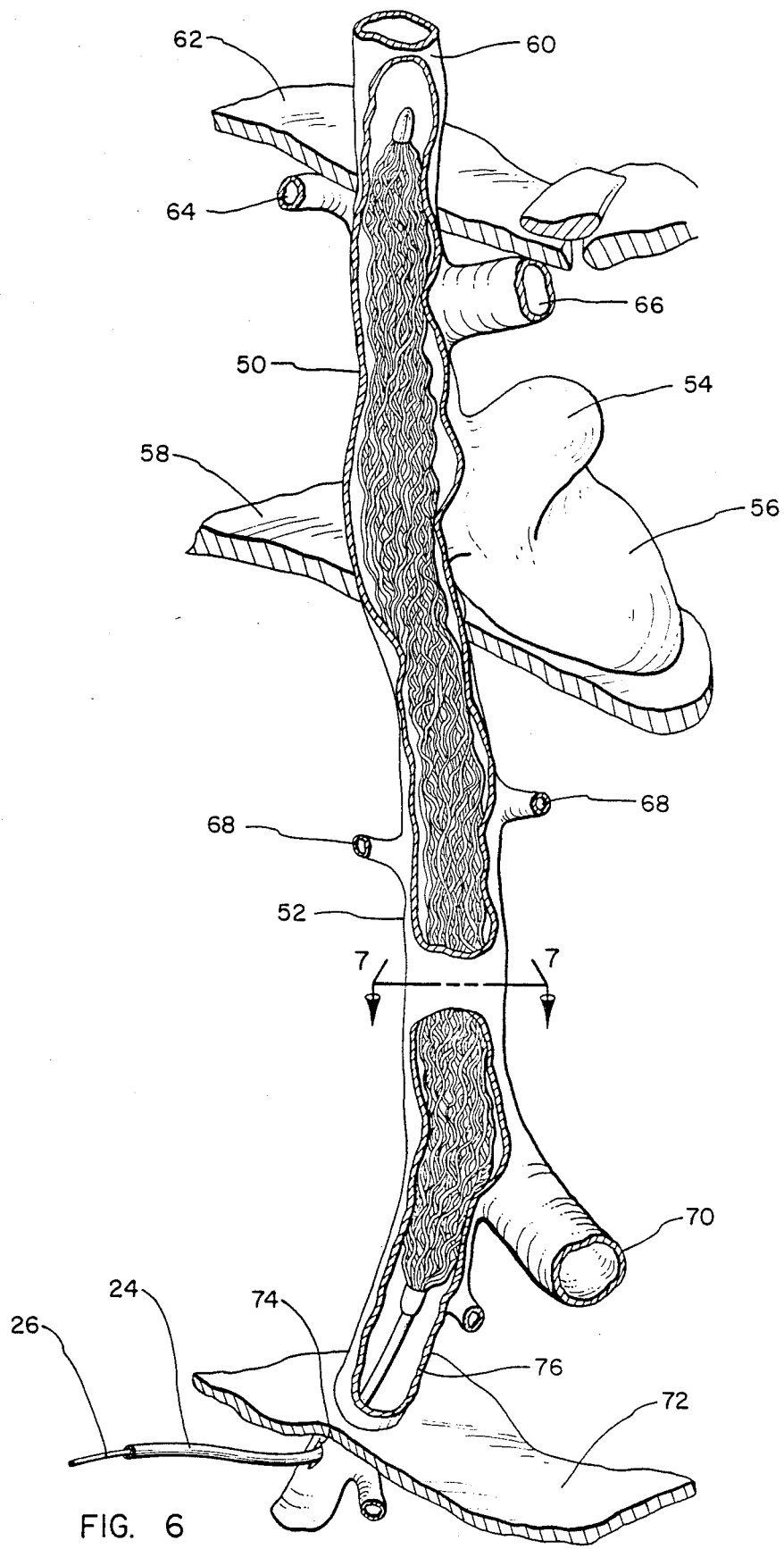
FIG. 6 is a perspective view of the embodiment illustrated in FIG. 2 positioned within the patient's venae cavae with a portion of the venae broken away.

Reference is now made to FIG. 6 wherein the method of using the present invention is illustrated. FIG. 6 specifically illustrates the placement of the present invention within venae cavae of a patient with reference to some internal human anatomy. Superior vena cava 50 and inferior vena cava 52 are shown in FIG. 6 as well as right atrium 54, right ventricle 56, and diaphragm 58. Also illustrated in FIG. 6 are jugular vein 60, clavicle 62, right subclavian vein 64, and innominate vein 66. In addition, FIG. 6 illustrates renal veins 68, left common iliac vein or internal jugular vein 70, and inguinal ligament 72.

As can be seen in FIG. 6, the apparatus 10 is inserted through a single incision 74 into the right external iliac, right femoral vein or right jugular vein. Prior to insertin within the venae cavae the overal diameter of the bundle of gas permeable tubes is reduced as best illustrated in FIG. 1. Diameter "A" of FIG. 1 represents a small insertion diameter of the gas permeable tubes. The insertion diameter is formed by twisting and elongating the gas permeable tubes as discussed above.

For safety reasons it is important to hydrate the gas permeable tubes and to remove any air bubbles which might remain between the individual tubes prior to inserting the device within the venae cavae.

Once the apparatus 10 is in place, inner lumen 26 preferably will be connected to a source of oxygen-enriched gas and outer lumen 24 preferably will be connected to a vacuum or some other exhaust means. As a result, oxygen-enriched gas will travel through the inner lumen 26 into distal chamber 30 and there into the distal ends 16 of the gas permeable tubes 12.

During the time the oxygen-enriched gas is within the gas permeable tubes it will be able to oxygenate the blood traveling through the venae cavae. In addition, carbon dioxide will be able to pass from the blood into the gas permeable tubes and thereby be removed from the blood stream. As discussed above, oxygen and carbon dioxide can readily travel through the walls of gas permeable tubes 12, but blood cannot enter the tubes. Thus, oxygenation can occur without the blood being directly exposed to gas bubbles.

After the gas has passed through the gas permeable tubes, the gas is released within proximal chamber 28. The distal end 25 of outer lumen 24 opens into proximal chamber 28. The gas enters the outer lumen and is removed from the device.

It is presently preferred that the device is operated at subatmospheric pressures. Currently, nearly 100% oxygen is introduced into the proximal end of inner lumen 26 at about atmospheric pressure. A vacuum is attached to the outer lumen 24 to provide the necessary pressure difference to cause the oxygen gas to flow through the gas permeable tubes. The oxygen gas experiences a pressure drop as it flows through the inner lumen 26 towards the distal chamber 30. As a result, the pressure of the oxygen gas as it enters the distal end 16 of the gas permeable tubes is subatmospheric.

Operation of the device at such low pressures will enhance carbon dioxide removal, yet also provide adequate blood oxygenation. The driving force behind blood gas transfer in the present invention is the difference between the partial pressures of the oxygen and carbon dioxide in the blood stream and the partial pressures of the oxygen and carbon dioxide in the gas permeable tubes. Lowering the pressure within the gas permeable tubes necessarily promotes transfer of carbon dioxide from blood into the gas permeable tubes. On the other hand, lowering the pressure within the gas permeable tubes reduces the partial pressure of oxygen in the gas permeable tubes. But because nearly pure oxygen is used, the partial pressure of oxygen is still sufficiently high to achieve adequate blood oxygenation.

Traditionally, blood oxygenation has been the primary goal in patients suffering from acute respiratory failure. However, it has been found that removal of carbon dioxide from blood is also important. Thus, operation of the device at subatmospheric pressures enhances the overall effectiveness of the device.

Moreover, since the operating pressure is preferably less than the blood pressure, any leak in the device cannot introduce air bubbles within the blood stream. Any such leak would introduce blood within the gas permeable tubes, rather than allow gas to enter the blood stream. Therefore, operation of the device at subatmospheric pressures provides significant safety benefits.

Although the above discussion has described oxygen being introduced through the inner lumen 26, it will be appreciated that the device can be also operated with oxygen being introduced through the outer lumen 24 and into the proximal chamber 28, with oxygen then flowing through the gas permeable tubes and into the distal chamber 30, and finally being removed through the inner lumen 26. Oxygen introduced through the outer lumen 24 is preferably at a subatmospheric pressure to compensate for the pressure drop across the inner lumen 26.

Similarly, the principles disclosed in connection with the present invention may readily be utilized in an extracorporeal blood gas exchange device. For example, blood removed from a patient could be simply passed through a large tube containing the present invention. As the blood flows past the gas permeable tubes, the blood is oxygenated and the blood releases carbon dioxide. The blood is then returned to the patient. Such extracorporeal use represents a substantial simplification of over existing extracorporeal methods.

In summary, the method and apparatus disclosed herein is a significant departure from the traditional extrapulmonary blood gas exchange systems of the prior art. In the present invention, only a single venous incision is required for inserting an extrapulmonary blood gas exchange device within the patient. In this way, oxygen is added to and carbon dioxide is removed from circulating blood without molesting, forcing, or irritating ailing or diseased lungs. In addition, the overall outside diameter of the apparatus may be adjusted to have a narrow diameter for insertion within the patient or adjusted to have an expanded diameter during blood oxygenation. As a result, blood surface contact with the gas permeable tubes is maximized, laminar blood flow through the venae cavae is inhibited and disturbed flow of blood over the tubes is achieved, thereby providing efficient blood gas exchange.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for effecting extrapulmonary blood gas exchange comprising:
    a plurality of gas permeable tubes, each tube having a first end and a second end;
    tube means comprising a first lumen and a second lumen, one of said first and second lumens extending between the first and second ends of the gas permeable tubes and the first lumen terminating adjacent to the first ends of the gas permeable tubes and the second lumen terminating adjacent to the second ends of the gas permeable tubes;
    means for introducing oxygen from the first lumen into the first end of the gas permeable tubes such that oxygen flows through the gas permeable tubes whereby blood in contact with the gas permeable tubes receives oxygen from the gas permeable tubes and releases carbon dioxide gas to the gas permeable tubes; and
    means for collecting carbon dioxide at the second ends of the gas permeable tubes and introducing said carbon dioxide into the second lumen for removal therethrough.

2. An apparatus as defined in claim 1, further comprising means for maintaining the gas permeable tubes in a spaced relation one from another such that blood surface contact with the gas permeable tubes is maximized and such that laminar blood flow between and around the gas permeable tubes is inhibited.

3. An apparatus as defined in claim 2, wherein said means for maintaining said spaced relation comprises a plurality of crimps along the length of the tubes.

4. An apparatus as defined in claim 1, wherein the means for introducing oxygen from the first lumen to the first ends of the gas permeable tubes comprises a first chamber providing an airtight enclosure around the first ends of said permeable tubes, and said first lumen terminating within said first chamber such that said first chamber thereby provides gaseous communication between the first lumen and the first ends of the gas permeable tubes.

5. An apparatus as defined in claim 1, wherein the means for collecting carbon dioxide at the second ends of the gas permeable tubes comprises a second chamber providing an airtight enclosure around the second ends of said gas permeable tubes, and said second lumen terminating within said second chamber such that said second chamber thereby provides gaseous communication between the second lumen and the second ends of the gas permeable tubes.

6. An apparatus as defined in claim 1, wherein the number of gas permeable tubes is from approximately 90 to approximately 1500.

7. An apparatus as defined in claim 1, wherein the gas permeable tubes have an outside diameter from approximately 200 microns to approximately 350 microns.

8. An apparatus as defined in claim 1, wherein one of said first and second lumens runs coaxially through the other.

9. An apparatus for effecting in vivo extrapulmonary blood gas exchange whereby blood flowing through the venae cavae of a patient receives oxygen and releases carbon dioxide, the apparatus comprising:
    a plurality of elongated gas permeable tubes, each tube having a first end and a second end;
    means for enclosing the first ends of the gas permeable tubes so as to form an airtight first chamber;
    means for enclosing the second ends of the gas permeable tubes so as to form an airtight second chamber; and
    a dual lumen tube having an outer lumen and an inner lumen which runs coaxially through said outer lumen, said outer lumen terminating and opening within the first chamber such that said outer lumen is in gaseous communication with the first ends of the gas permeable tubes, said inner lumen terminating and opening within the second chamber such that said inner lumen is in gaseous communication with the second ends of the gas permeable tubes.

10. An apparatus as defined in claim 9 further comprising means for selectively adjusting the overall diameter of the gas permeable tubes so as to be able to adjust said diameter to provide either an insertion diameter when inserting said apparatus into the venae cavae, or an oxygenation diameter after said apparatus is in place within the venae cavea.

11. An apparatus as defined in claim 10, further comprising means for binding the gas permeable tubes together at each end, wherein the inner lumen is nonrotatably anchored to the binding means of said second ends and the outer lumen in nonrotatably anchored to the binding means of said first ends.

12. An apparatus as defined in claim 11, wherein the means for selectively adjusting said overall diameter comprises means for engaging the distal end of the inner lumen and means for twisting the gas permeable tubes while holding the binding means at one of the first and second ends essentially stationary relative to the other.

13. An apparatus as defined in claim 12, wherein said means for engaging the end of the inner lumen comprises a stylet removably inserted through the inner lumen.

14. An apparatus as defined in claim 13, wherein said means for twisting the gas permeable tubes comprises a stationary member removably attached to the outer lumen, a twisting member rotatably engaged with said stationary member, and means for selectively securing the stylet to said twising member, such that twisting of said twisting member relative to said stationary member while the stylet is secured thereto twists the gas permeable tubes while holding the binding means at one of the first and second ends essentially stationary relative to the other.

15. An apparatus as defined in claim 14, further comprising a spacer lumen nonrotatably anchored to the binding means of said first and second ends, said spacer lumen being coaxial with said inner lumen such that said inner lumen runs coaxially through said spacer lumen.

16. An apparatus as defined in claim 15, wherein the spacer lumen is flexible enough to permit the spacer lumen to be twisted about its longitudinal axis as the binding means at one of the first and second ends is twisted relative to the other such that when so twisted and held in the twisted position, the spacer lumen provides a spring-like action for untwisting the gas permeable tubes to automatically provide said oxygenation diameter when said stylet is released from the twisting member.

17. An apparatus as defined in claim 14 wherein said stationary member comprises a first port means for introduction of oxygen therethrough to said outer lumen, and second port means communicating with said inner lumen and adapted for connection to a source of suction so as to provide evacuation of the carbon dioxide through said inner lumen.

18. An apparatus as defined in claim 9, further comprising means for maintaining the gas permeable tubes in a spaced relation one from another such that blood surface contact with the gas permeable tubes is maximized and such that laminar blood flow between and around the gas permeable tubes in inhibited.

19. An apparatus as defined in claim 18, wherein the means for maintaining said spaced relation comprises a plurality of crimps along the length of the tubes.

20. An apparatus as defined in claim 9, wherein the number of gas permeable tubes is from approximately 90 to approximately 1500.

21. An apparatus as defined in claim 9, wherein the gas permeable tubes have an outside diameter from approximately 200 microns to approximately 350 microns.

22. An apparatus for effecting in vivo extrapulmonary blood gas exchange whereby blood flowing through the venae cavae of a patient receives oxygen and releases carbon dioxide, the apparatus comprising:
  a plurality of elongated gas permeable tubes, each tube having a distal and a proximal end;
  means for binding the gas permeable tubes together at each end, such that the bound gas permeable tubes at said ends define an overall diameter sufficiently small to permit insertion within the venae cavae of a patient;
  a dual lumen tube having an outer lumen and an inner lumen which runs coaxially through said outer lumen, said outer lumen terminating adjacent the proximal ends of the gas permeable tubes and said inner lumen terminating adjacent the distal ends of the gas permeable tubes;
  means for enclosing the bound proximal ends of the gas permeable tubes so as to form an airtight first chamber enclosing said proximal ends together with one end of the outer lumen such that the outer lumen is thereby in gaseous communication with the proximal ends of the permeable tubes;
  means for enclosing the bound distal ends of the gas permeable tubes so as to form an airtight second chamber enclosing said distal ends with one of said inner lumen such that the inner lumen is thereby in gaseous communication with the distal ends of the gas permeable tubes; and
  means for selectively adjusting the diameter of the gas permeable tubes so as to be able to adjust said diameter to provide either an insertion diameter when inserting said apparatus within the venae cavae, or an oxygenation diameter after said apparatus is in place within the venae cavae.

23. An apparatus as defined in claim 22 further comprising means for maintaining the gas permeable tubes in a spaced relation one from another when inserted in the venae cavae and when configured with said oxygenation diameter, whereby blood surface contact with the gas permeable tubes is maximized and laminar blood flow between and around the gas permeable tubes in inhibited.

24. An apparatus as defined in claim 23, wherein the means for maintaining said spaced relation comprises a plurality of crimps along the length of the tubes.

25. An apparatus as defined in claim 22, wherein the means for selectively adjusting said diameter comprises means for engaging the end of the inner lumen which opens into the second chamber, and means for twisting the gas permeable tubes while holding the binding means at one of the first and second ends essentially stationary relative to the other.

26. An apparatus as defined in claim 25, wherein the means for engaging the end of said inner lumen comprises a stylet removably inserted through the inner lumen.

27. An apparatus as defined in claim 26, wherein said means for twisting the gas permeable tubes comprises a stationary member removably attached to the outer lumen, a twisting member rotatably engaged with said stationary member, and means for selectively securing the stylet to said twisting member, such that twisting of said twisting member relative to said stationary member while the stylet is secured thereto twists the gas permeable tubes while holding the binding means at one of the first and second ends essentially stationary relative to the other.

28. An apparatus as defined in claim 27, further comprising a spacer lumen nonrotatably anchored to the binding means of said first and second ends, said spacer lumen being coaxial with said inner lumen such that said inner lumen runs coaxially through said spacer lumen.

29. An apparatus as defined in claim 28, wherein the spacer lumen is flexible enough to permit the spacer lumen to be twisted about its longitudinal axis as the binding means at one of the first and second ends is twisted relative to the other such that when so twisted and held in the twisted position, the spacer lumen provides a spring-like action for untwisting the gas permeable tubes to automatically provide said oxygenation diameter when said stylet is released from the twisting member.

30. An apparatus as defined in claim 29, wherein said stationary member comprises a first port means for introduction of oxygen therethrough to said outer lumen, and second port means communicating with said inner lumen and adapted for connection to a source of suction so as to provide evacuation of the carbon dioxide through said inner lumen.

31. An apparatus as defined in claim 22, wherein the number of gas permeable tubes is from approximately 90 to approximately 1500.

32. An apparatus as defined in claim 31, wherein the gas permeable tubes have an outside diameter from approximately 200 microns to approximately 350 microns.

33. A method for effecting in vivo extrapulmonary blood gas exchange comprising the steps of:
  reducing the overall diameter of a plurality of gas permeable tubes to form an overall insertion diameter with respect to said plurality of tubes;

inserting the gas permeable tubes within the venae cavae of a patient through a single venous incision sized to accommodate said insertion diameter;

enlarging the overall diameter of said plurality of gas permeable tubes once they are within said venae cavae to from an oxygenation diameter; and passing oxygen enriched gas through the gas permeable tubes at subatmospheric pressure such that blood flowing through the venae cavae is oxygenated as carbon dioxide is removed from the blood into the gas permeable tubes.

34. A method as defined in claim 33 further comprising the step of maintaining the gas permeable tubes in a spaced relation one from another when said oxygenation diameter is formed so that blood surface contact with the gas permeable tubes is maximized and such that laminar blood flow in and around the gas permeable tubes in inhibited.

35. A method as defined in claim 33, wherein the step of inserting the gas permeable tubes within the venae cavae comprises the steps of:

positioning an introducer within said incision;

hydrating the gas permeable tubes within an aqueous solution to completely remove any bubbles adhering to the surface of the gas permeable tubes; and passing the gas permeable tubes through the introducer and into the venae cavae of a patient.

36. A method as defined in claim 33, wherein said gas permeable tubes are comprised of inlet ends and outlet ends, said inlet ends being in gaseous communication with one of an outer and an inner lumen and the outlet ends being in gaseous communication with the other said lumen, said inner lumen running coaxially through said outer lumen, and wherein the step of reducing the diameter of the gas permeable tubes comprises the steps of:

inserting a stylet through said inner lumen so as to engage the distal end of the inner lumen; and twisting the stylet while holding the inlet ends of the gas permeable tubes essentially stationary relative to the outlet ends of said tubes so that the gas permeable tubes are twisted tightly together to form said insertion diameter.

37. A method as defined in claim 36, wherein the step of enlarging the diameter of the gas permeable tubes comprises the steps of:

untwisting the stylet so that the gas permeable tubes are untwisted and unspaced apart from each other to form an oxygenation diameter; and removing the stylet from the inner lumen.

* * * * *

UNITED STATES PATENT AND TRADEMARK OFFICE
CERTIFICATE OF CORRECTION

PATENT NO. : 4,850,958

DATED : July 25, 1989

INVENTOR(S) : Gaylord Berry et al.

It is certified that error appears in the above-identified patent and that said Letters Patent is hereby corrected as shown below:

```
Column 1, line 18, "obstuuction" should be --obstruction--
Column 1, line 20, "aliments" should be --ailments--
Column 1, line 42, "capaable" should be --capable--
Column 2, line 26, "canae" should be --cavae--
Column 2, line 46, "sprial" should be --spiral--
Column 4, line 19, "effecient" should be --efficient--
Column 5, line 68, "and airtight" should be --an airtight--
Column 12, line 36, "cavea" should be --cavae--
Column 14, line 25, "statioinary" should be --stationary--
```

Signed and Sealed this

Twelfth Day of June, 1990

Attest:

HARRY F. MANBECK, JR.

*Attesting Officer*           *Commissioner of Patents and Trademarks*

UNITED STATES PATENT AND TRADEMARK OFFICE
CERTIFICATE OF CORRECTION

PATENT NO. : 4,850,958
DATED : July 25, 1989
INVENTOR(S) : Gaylord Berry et al.

It is certified that error appears in the above-identified patent and that said Letters Patent is hereby corrected as shown below:

Column 3, lines 57-57, delete second occurrence of "or internal jugular vein"
Column 7, line 36, "it" should be --if--
Column 7, line 48, "cuylindrical" should be --cylindrical--
Column 13, claim 22, line 59, after "one" insert --end--

Signed and Sealed this

Seventh Day of September, 1993

Attest:

BRUCE LEHMAN

*Attesting Officer*  *Commissioner of Patents and Trademarks*